United States Patent [19]
Wood et al.

[11] Patent Number: 5,990,153
[45] Date of Patent: Nov. 23, 1999

[54] ULTRASONICATED α-LIPOIC ACID SOLUTIONS FOR ATTENUATING MICROVASCULAR INJURY

[76] Inventors: John G. Wood, 20922 W. 63rd Terrace, Shawnee, Kans. 66218; Frederick E. Samson, 171 Lake Shore S., Lake Quivira, Kans. 66106-9516

[21] Appl. No.: 09/072,848

[22] Filed: May 5, 1998

Related U.S. Application Data

[60] Provisional application No. 60/046,838, May 5, 1997.

[51] Int. Cl.[6] .................................................. A61K 31/385
[52] U.S. Cl. ............................................ 514/440; 252/302
[58] Field of Search .............................. 514/440; 252/302

[56] References Cited

U.S. PATENT DOCUMENTS

| | | | |
|---|---|---|---|
| 5,318,987 | 6/1994 | Weithmann et al. | 514/457 |
| 5,498,427 | 3/1996 | Menasche | 424/678 |
| 5,532,269 | 7/1996 | Koltringer | 514/440 |
| 5,650,429 | 7/1997 | Conrad et al. | 514/440 |

FOREIGN PATENT DOCUMENTS

| | | |
|---|---|---|
| 4138040 A1 | 5/1992 | Germany . |
| 1769865 A1 | 10/1992 | U.S.S.R. . |

OTHER PUBLICATIONS

Remington's Pharmaceutical Sciences, 18th edition, Mack Pub. (Easton, PA), 1508, 1538, 1990.

Arai et al., Drug Design and Delivery 2(2), 109–20, Dec. 1987.

Schöheit et al., "Effect of α–Lipoic Acid and Dihydrolipoic Acid on Ischemia/ Reperfusion Injury of the Heart and Heart Mitochondria," *Biochimica et Biophysica Acta*, 1271:335–342 (1995).

Werker et al., "Neither Desferrioxamine Nor Lipoic Acid Enhances the Cold Ischaemic Tolerance of Epigastric Free Flaps in Rats," *Microsurgery*, 14:574–578 (1993).

Ou et al., "Thioctic (Lipoic) Acid: A Therapeutic Metal–Chelating Antioxidant?" *Biochemical Pharmacology*, 50(1):123–126 (1995).

Lester Packer, "Antioxidant Properties of Lipoic Acid and Its Therapeutic Effects in Prevention of Diabetes Complications and Cataracts[a]," *Annals New York Academy of Sciences*, 738:257–264 (Nov. 17, 1994).

Barbiroli et al., "Lipoic (Thioctic) Acid Increases Brain Energy Availability and Skeletal Muscle Performance as Shown by In Vivo $^{31}$P–MRS in a Patient with Mitochondrial Cytopathy," *Journal of Neurology*, 242: 472–477 (1995).

Müller et al., "Prolonged Pretreatment with α–Lipoic Acid Protects Cultured Neurons Against Hypoxic, Glutamate–, or Iron–Induced Injury," *Journal of Cerebral Blood Flow and Metabolism*, 15(4):624–630 (1995).

Sandhya et al., "Role of DL α–Lipoic Acid in Gentamicin Induced Nephrotoxicity," *Molecular and Cellular Biochemistry*, 145:11–17 (1995).

Werker et al., "Oxidative Processes and Free Radical Scavengers in Ischaemia–Reperfusion Injury in Adipocutaneous Flaps: In Vitro Lipid Peroxidation Assessment," *British Journal of Plastic Surgery*, 48(8):590–596 (Dec. 1995).

Nickander et al., "Alpha–Lipoic Acid: Antioxidant Potency Against Lipid Peroxidation of Neural Tissues In Vitro and Implications for Diabetic Neuropathy," *Free Radical Biology & Medicine*, 21(5):631–639 (1996).

Wood et al., "Attenuation of Hemorrhagic Shock–Induced Microvascular Dysfunction By α–Lipoic Acid," *The Oxygen Society*, (Nov. 1996).

*Primary Examiner*—Phyllis G. Spivack
*Attorney, Agent, or Firm*—Sonnenschein Nath & Rosenthal

[57] ABSTRACT

A pharmaceutical composition comprising an ultrasonicated formulation of α-lipoic acid and an aqueous solution which may also contain other antioxidants and/or metal chelators is disclosed.

Also disclosed is a method of ultrasonically preparing pure or mixed micelles of lipid-soluble antioxidants and α-lipoic acid in aqueous solutions for intravenous delivery to mitigate microvascular dysfunction in hemorrhagic shock and other conditions of acute microvascular injury.

16 Claims, 5 Drawing Sheets

ULTRASONICATED α-LIPOIC ACID SOLUTIONS FOR ATTENUATING MICROVASCULAR INJURY

RELATED APPLICATION

This application is based on a provisional patent application Serial No. 60/046,838 filed May 5, 1997.

FIELD OF THE INVENTION

This invention pertains to the prevention and treatment of mammalian blood vessel injury. More particularly, this invention relates to an ultrasonication method of solubilizing highly lipophilic antioxidants, such as α-lipoic acid, for delivery to the lipid membranes of microvascular cells where such antioxidants mitigate vascular dysfunction following a variety of systemic insults, such as hemorrhagic shock.

BACKGROUND OF THE INVENTION

Hemorrhagic shock is the clinical condition of inadequate perfusion (ischemia) of the tissues as a result of blood loss. The treatment of hemorrhagic shock requires prompt restoration of tissue perfusion by infusing large volumes of lactated Ringer's solution, saline, albumin solutions, whole blood, dextran, or solutions containing stabilized hemoglobin. Despite prompt restoration of intravascular volume, the morbidity and mortality due to hemorrhagic shock remain unacceptably high.

A key reason for the frequent failure of fluid resuscitation in hemorrhagic shock is the generalized and progressive microvascular injury which is a consequence of tissue ischemia. The microvasculature consists of venules, arterioles and their intervening capillary bed. Following a period of ischemia and reperfusion (as occurs in hemorrhagic shock followed by fluid resuscitation), the capillaries and venules become excessively permeable and the arterioles constrict. The leaking of blood proteins from the excessively permeable venules into the tissue interstitium causes additional fluid loss and edema (swelling), which further compromises blood flow and leads to organ dysfunction. Arteriolar constriction results in areas of persistent tissue ischemia and local hypoxia. Because of a forced state of anaerobic metabolism resulting in lactic acid accumulation and tissue acidosis, hemorrhagic shock may be followed by multiple organ failure and death several days after prompt and seemingly successful restoration of circulating volume sufficient to reperfuse vital organs.

In addition to the arteriolar constriction and the increased permeability of venules, a third factor in microvascular dysfunction is the adhesion of circulating white blood cells (leukocytes) to venular endothelial cells. Adherent leukocytes release proteolytic enzymes, inflammatory mediators and reactive oxidants, all of which further accelerate the cascade of microvascular injury. Leukocytes, specifically polymorphonuclear neutrophils and monocytes, originate in bone marrow. From this location they enter the general circulation and adhere to post-capillary venules at sites of the inflammatory response. They initially adhere to the endothelial surface of these venules and eventually migrate across the vessel wall into the tissues. The process of leukocyte recruitment into an area of inflammatory response begins with margination of leukocytes to the slower peripheral section of the bloodstream. At this stage the leukocytes loosely adhere to the endothelium, and this weak binding results in "rolling" of the leukocytes along the vessel wall. In this sense, the leukocytes sample the local environment and are fully arrested if the appropriate signals are received, resulting in stronger adhesive interactions. Following firm adhesion, the leukocytes transmigrate across the endothelial wall. They then continue through the tissues to sites of inflammation where they play a key role in killing of bacteria. Leukocyte adhesion is an early sign of microvascular injury which occurs during the body's response to injury or infection. When the microvascular injury is localized to a small area, there are usually no adverse effects to the person. However, when generalized microvascular injury occurs throughout the body, vascular permeability may be impaired to such an extent that organ injury and death result.

At a molecular level, an important cause of microvascular injury following hemorrhagic shock is the generation of highly reactive oxidants. These toxic species are formed in ischemic tissues following the reintroduction of oxygen when perfusion has been restored by fluid resuscitation. One critical location of oxidant generation responsible for microvascular injury is the endothelial cell, a single layer of which forms the inner lining of all blood vessels. Endothelial cells actively regulate microvascular function through the production of several vasoactive substances, including nitric oxide (NO).

Nitric oxide's normal role is to regulate the degree of constriction of the microvessels, their permeability and to inhibit the adhesion of circulating leukocytes. When NO levels decrease below normal, arterioles constrict, venules become permeable, and leukocytes adhere to venular walls. Reactive oxidants, such as the superoxide radical, may trigger microvascular dysfunction by reacting with NO to form peroxynitrite, which is even more toxic than the superoxide radical. The net decrease in microvascular NO resulting from this reaction may be a key cause of the arteriolar constriction, as well as the increased venular permeability and leukocyte adhesion seen in the setting of ischemia/reperfusion.

Because oxidant species play a central role in microvascular dysfunction, investigators have experimented with antioxidants as a way of mitigating the effects of reactive oxidants. Superoxide dismutase (SOD), catalase, and the iron binding molecule deferoxamine have been tried in resuscitation fluids after hemorrhagic shock with limited success. Adverse side effects or poor lipid solubility have been proposed to explain why some agents capable of destroying reactive oxidants in vitro have proven less effective in a living organism. High lipid solubility is a crucial characteristic of a clinically effective antioxidant because oxidant generation takes place within the cells, for example, within mitochondria which are intracellular organelles inside of the endothelial cells. A rapid, passive diffusion of antioxidants is possible only if the antioxidant can pass through the lipid membranes investing the endothelial cells and their mitochondria.

The ideal antioxidant for mitigating ischemia/reperfusion microvascular injury would be one which is lipid soluble and non-toxic. α-lipoic acid is a lipid soluble antioxidant which naturally occurs in the body. Even in the pharmacological doses given to patients with diabetic peripheral nerve disease, α-lipoic acid has been administered safely and without long term side effects.

Alpha-lipoic acid, in addition to its non-toxicity and lipophilicity, has the advantage of being rapidly converted in tissues into its reduced form, dihydrolipoic acid (DHLA). DHLA also has potent antioxidant effects. Further, both α-lipoic acid and DHLA can disarm oxidants through a variety of mechanisms including free radical quenching, metal chelation, and regeneration of other common natural antioxidants.

Because resuscitation fluids—saline, dextran, blood, stabilized hemoglobin solutions—are all aqueous solutions, a problem with lipid soluble antioxidants, such as α-lipoic acid is its poor water solubility. The solubility may be enhanced by adding benzyl alcohol or DMSO, but such solvents introduce additional side effects and potential toxicities. The present invention overcomes the problem of delivering a lipophilic antioxidant in an aqueous resuscitation fluid by a method of ultrasonic solubilization which forms a stable micellular solution of α-lipoic acid. The utility of the inventive method described herein will be illustrated in protocols showing the effect of ultrasonicated aqueous solutions of α-lipoic acid and other antioxidants on leukocyte adhesion, venular permeability and arteriolar constriction, following ischemia/reperfusion.

Previous methods of delivering antioxidants which are lipophilic to the tissues involve solubilizing the antioxidant in solvents such as benzyl alcohol, DMSO, or other chemicals. Not only does the presence of such solvents have the potential to introduce toxicities which may exacerbate microvascular injury, but their presence confuses the interpretation of any protocol designed to evaluate antioxidant effects.

The present invention seeks to overcome these limitations by solubilizing α-lipoic acid in aqueous solution without the use of additional solvents. α-lipoic acid and other antioxidants are rendered soluble in aqueous solutions by the use of ultrasonication. Because the α-lipoic molecule contains a polar (water soluble) carboxy-acid group and a non-polar, lipid soluble chain of carbon and sulfur atoms, the molecule is amphipathic, i.e., it has the ability to form micelles. Micelles may be formed in aqueous solution if a molecule possesses both polar and non-polar groups. After ultrasonication the polar, water soluble ends of the α-lipoic acid molecule are on the outside of aggregations of α-lipoic acid. The non-polar, lipid soluble tails are directed inward forming a tiny droplet, a micelle, which is water soluble. Ultrasonication of amphipathic molecules into micelles such as can be done with α-lipoic acid also has the possibility of creating mixed micelles. In this manner a mixture of α-lipoic acid with other antioxidants, which may not have the ability to form micelles alone for lack of any polar group, can be contained within a micelle of α-lipoic acid. In this way, mixed micelles containing α-lipoic acid and purely non-polar but highly lipid soluble antioxidants can be used to convey antioxidants to the tissues.

There are numerous other clinical conditions besides hemorrhagic shock which have as their final common pathway oxidant-inducing injury to tissues which can be treated and/or prevented with the inventive solutions. These conditions are described below.

SUMMARY OF THE INVENTION

To overcome limitations of poor membrane penetration and poor solubility of lipophilic antioxidants in aqueous solution, the present invention uses an ultrasonication method to dissolve crystalline α-lipoic acid in an aqueous resuscitation fluid. The present invention uses α-lipoic acid alone or in combination with other antioxidants and/or metal chelators.

Accordingly, a principal object of the present invention is the formulation of parenteral compositions useful for preventing and treating microvascular injury in mammals.

A further object of the invention is to provide a method for solubilizing lipophilic antioxidants in pure or mixed micelles in aqueous solutions such as normal saline, D5W, lactated Ringer's, albumin-containing solutions, dextran resuscitation fluids, stabilized hemoglobin-containing resuscitation fluids, or the like.

DESCRIPTION OF THE PREFERRED EMBODIMENTS

The formulation of the present invention is prepared by adding approximately 20 mg or other therapeutically effective amount of α-lipoic acid, preferably a racemic mixture of the D- and L- enantiomers (crystalline DL-6, 8-thioctic acid, Sigma, St. Louis, Mo.) to approximately 40 ml of normal saline resulting in a concentration of 0.5 mg of α-lipoic acid per ml. This formulation is then ultrasonicated for about 90 to 240 seconds using a Fisher Scientific Model FS60 ultrasonicator probe or the like to form a microscopic micellar suspension of the lipophilic lipoic acid in saline. In lieu of normal saline, other pharmaceutically acceptable solutions may be utilized including, but not limited to, 0.9% saline solution, 5% dextrose solution, lactated Ringers solution, 5% dextrose in lactated Ringer's solution, dextrose-saline combinations, albumin-containing solutions, dextran, dextran-saline combinations, and stabilized hemoglobin-containing resuscitation fluids. The resulting antioxidant solution is then administered parenterally to the patient suffering from one or more of the below-mentioned diseases in a pharmacologically effective amount. See "The Broader Context of Oxidant-Induced Tissue Injury," below.

To the inventive antioxidant formulation, additional antioxidants and/or metal chelators may optionally be added to pharmacologically enhance the formulation. The additional antioxidants are first separately ultrasonicated in an aqueous solution as above and then added to the α-lipoate formulation to form a solution of mixed micelles ready for intravenous administration. Alternatively, the α-lipoic acid and additional antioxidant may be contemporaneously ultrasonically homogenized in the aqueous solution. Examples of additional antioxidants include catalase, superoxide dismutase, selenium, alpha-tocopherol, nitrones and N-acetylcysteine, and are added in any pharmacologically effective concentration. For example, Applicants have successfully formulated 5% micellar solutions of catalase and superoxide dismutase.

Metal chelators such as deferoxamine (DESFERAL® MESYLATE) may also be separately or contemporaneously ultrasonically homogenized as above to be administered with the inventive α-lipoate formulations. Preferably, deferoxamine is incorporated at a concentration of 5%. Other chelators useful in the inventive formulations include urates or other parenterally administered chelators.

The Broader Context of Oxidant-induced Tissue Injury

Hemorrhagic shock is the classic model of ischemia/reperfusion induced microvascular dysfunction. As stated, the molecular basis of injury appears related to generation of toxic reactive oxidants, such as the superoxide radical in the mitochondria of the endothelial cells lining the microvessels. Oxidant-induced microvascular dysfunction is not limited to hemorrhagic shock, however, and the inventive solutions are useful for the treatment and prevention of many other oxidant-induced disease states besides hemorrhagic shock. There are numerous other clinical conditions which have as their final common pathway oxidant-induced injury to tissues which can be treated and/or prevented with the inventive solutions. These include:

a. In the setting of brain injury, oxidative damage by free radicals, excitatory amino acids and iron are likely mechanisms of damage following ischemia. Brain ischemia may be the result of hemorrhagic shock, but it also occurs in the setting of stroke. One type of stroke involves occlusion of vessels by blood clots; if the clot later moves or there is an alternative supply of blood to the region, the ischemic area may be reperfused. The ischemia/reperfusion injury of neurons (brain cells) cultured in vitro can be mitigated by α-lipoic acid pretreatment.

b. In the setting of kidney damage (nephrotoxicity) by aminoglycoside antibiotics such as gentamicin, toxic oxidants may damage the glucose transport molecules of certain cell membranes in the kidneys, leading to loss of this vital source of energy and ultimately cell death. Nephrotoxicity by gentamicin can be reduced by α-lipoic acid.

c. In the setting of peripheral nerve disease in diabetes mellitus, peroxidation of lipids in nerve membranes by oxidizing free radicals is a likely mechanism of injury. α-lipoic acid in both nerve and brain reduces in vitro lipid peroxidation in a dose-dependent manner.

d. In the setting of heart ischemia/reperfusion, as may be seen in the setting of heart transplant or following myocardial infarction, the generation of toxic oxygen free radicals is a likely cause of rhythm disturbances and heart stunning. In both isolated hearts and isolated heart mitochondria following global ischemia and reperfusion, α-lipoic acid and DHLA exerts beneficial effects in a dose-dependent manner.

e. In the setting of plastic surgery where free flaps of tissue are used for reconstructing lost or injured body parts, the excised flaps are necessarily subjected to a period of ischemia followed (on reattachment) to reperfusion. In this setting, oxygen derived free radicals likely play a role in subsequent tissue injury, leading to cellular death and loss of the graft.

f. In the setting of cataracts, oxidation injury probably plays a role in lens damage; the lens is highly susceptible to oxygen radicals or their derivatives. Lipoic acid, possibly by interaction with antioxidants such as vitamin C (ascorbic acid) and vitamin E (α-tocopherol), may be protective against development of cataracts in an animal model of induced low levels of the natural antioxidant glutathione.

g. In the setting of nicotine-induced platelet adhesion of blood vessels and prevention of vascular injury in diabetics and smokers, U.S. Pat. No. 5,532,269 of Koltringer (1995) teaches the use of oral α-lipoic acid. In the acute setting of hemorrhagic shock, however, an oral agent cannot be administered safely to patients, as consciousness is usually impaired. Furthermore, high levels of antioxidant must be delivered rapidly to the vascular beds following shock, which can only occur after IV administration.

h. In the setting of oxygen carrying resuscitation fluids, cell free stabilized hemoglobin preparations are under investigation. These solutions offer the advantage of replacing volume and therefore improving tissue perfusion while at the same time carrying oxygen bound to the hemoglobin to the tissues. Being acellular, there is no risk of a tissue mismatch (transfusion reaction) and no need to cross-match the product against the patient's blood as must be done with whole blood transfusion. The disadvantage of hemoglobin-containing solutions is that they increase the delivery of oxygen to recently ischemic tissue and therefore may enhance oxidative injury by the generation of oxygen free radicals. Also, nitric oxide binds tightly to hemoglobin thereby reducing endothelial NO levels, and exacerbating the cascade of oxidative injury. These latter features of hemoglobin may be the major limitation in the use of such solutions, unless some additive, such as α-lipoic acid or other antioxidants, can be added to counteract the harmful oxidative effects of the hemoglobin.

i. In the setting of adult respiratory distress syndrome (ARDS), free radical injury to pulmonary tissues, including the microvasculature, likely plays an important role in the pathogenesis of the condition. After a lung insult such as pneumonia, ischemic lung vessels begin to leak protein fluid into the interstitial spaces of the lung. The resulting edema significantly impairs oxygen transport leading to decreased oxygen levels in the blood and increased stiffness (noncompliance) of the lung tissue. These alterations necessitate an increased need for high mechanical ventilation pressures and high levels of inspired oxygen, both of which may further increase lung injury. ARDS is associated with a high morbidity and survivors often are pulmonary cripples. The use of antioxidants in this setting has the potential to mitigate the tissue injury seen in ARDS and also in the treatment of ARDS with high oxygen levels.

j. Sepsis and multi-organ failure also can be initiated by oxidative injury to the microvasculature. Initially the syndrome may be triggered by bacteria which in turn initiate a cell mediated inflammatory response which damages the microvasculature. Multi-organ failure can also be seen after hemorrhagic shock, a setting in which infection may or may not play a role. When it does, the altered permeability of blood vessels may permit the entry of bacteria into the bloodstream triggering overwhelming sepsis.

The foregoing conditions are discussed here to illustrate that toxic reactive oxidants represent a final common pathway for many seemingly diverse clinical conditions. Many of these conditions involve the endothelial cells of the microvasculature, such as hemorrhagic shock, ARDS, multi-organ failure, stroke, myocardial infarction, flap grafts, hemoglobin containing resuscitation fluids, nicotine abuse, and diabetes. Others involve injury to other cells membranes such as the lipid membranes of nerves or the glucose transport enzymes as in diabetic nephropathy, cataracts, or aminoglycoside nephrotoxicity.

The foregoing examples are illustrative of the many ways that free radical toxicity plays a role in diverse disease states. Because the toxicity of oxidizing agents can be mitigated by antioxidants, those having skill in the art will understand that the methods described herein for the antioxidant treatment of hemorrhagic shock are equally applicable to other clinical conditions having oxidative injury as their final common pathway.

EXAMPLES

To demonstrate the efficacy of ultrasonically solubilized antioxidants and chelators, animals subjected to hemorrhagic shock were treated with α-lipoic acid, additional antioxidants and/or metal chelators in the resuscitation fluids to mitigate microvascular injury, were exposed to other agents capable of causing vascular injury, and then were analyzed. Three protocols are described herein to demonstrate the effects of α-lipoic acid, additional antioxidants and/or chelators prepared according to this invention. The first illustrates the effect of the inventive composition on leukocyte adhesion after ischemia/reperfusion (hemorrhagic shock) by performing direct microscopic visualization of venules using intravital microscopy.

The second protocol demonstrates the effects of α-lipoic acid, additional antioxidants and/or chelators on venular permeability after ischemia/reperfusion utilizing a fluorescent-labeled protein (FITC-labeled albumin). The inventive formulation prevents the leakage of these proteins into the interstitial tissues.

The third protocol demonstrates the effect of α-lipoic acid, additional antioxidants and/or chelators on arteriolar constriction after ischemia/reperfusion using a constant flow perfused stomach to demonstrate antioxidant effects on vascular reactivity (arteriolar dysfunction).

The advantage of the foregoing protocols to demonstrate the effects of the inventive formulations in the setting of microvascular injury is their ability to directly demonstrate the effects on the microvasculature in the living animal immediately during and after the vascular insult. In the protocols, the microvascular responses were videotaped and simultaneously subjected to measurements of microvascular size, flow, leukocyte adhesion, and vascular permeability to FITC albumin. Specifically, the method of ultrasonic solubilization permits lipid soluble antioxidants to be delivered to critical sites within the microvasculature, specifically to the mitochondria, to ameliorate the destructive effects of the toxic oxidants formed during ischemia and reperfusion as is seen in hemorrhagic shock followed by fluid resuscitation.

For purposes of the demonstrative protocols, male Sprague Dawley rats weighing 250 to 300 gm. were used.

General Animal Preparation for Leukocyte Adhesion and Venular Permeability Protocols After an overnight fast with free access to water, rats were injected IM with urethane (1.5 gm. per km.). During all procedures, the animal's temperature was maintained at 36° to 38° C. using a homeothermic blanket system connected to an intrarectal temperature probe. Polyethylene cannulas were inserted into the jugular vein, femoral artery, and carotid artery. Fluids or drugs were infused via the jugular vein while blood pressure was continuously monitored using the femoral artery cannual connected to a digital blood pressure monitor. The femoral artery catheter was used for removal of blood to lower blood pressure from the normal value of approximately 100 to 115 mmHg to shock levels of 30 mmHg.

After urethane anesthesia, the abdomen of the rat was surgically opened to expose a portion of the mesentery. The animal was positioned on a plexiglass sheet on top of the stage of an inverted microscope. A section of the small intestine was extended and positioned over a glass cover slip on a plexiglass sheet in order to view a mesenteric venule. The mesentery was superfused at 2 ml. per minute with bicarbonate-buffered saline at 37° C. and pH 7.4 which was aerated with 95% nitrogen and 5% $CO_2$ to reduce the oxygen tension in the buffer. Images of mesenteric venules (40× objective, 1OX eyepiece) were recorded on a videocassette recorded with a time date generator using an ICCD camera.

Figure 1A:
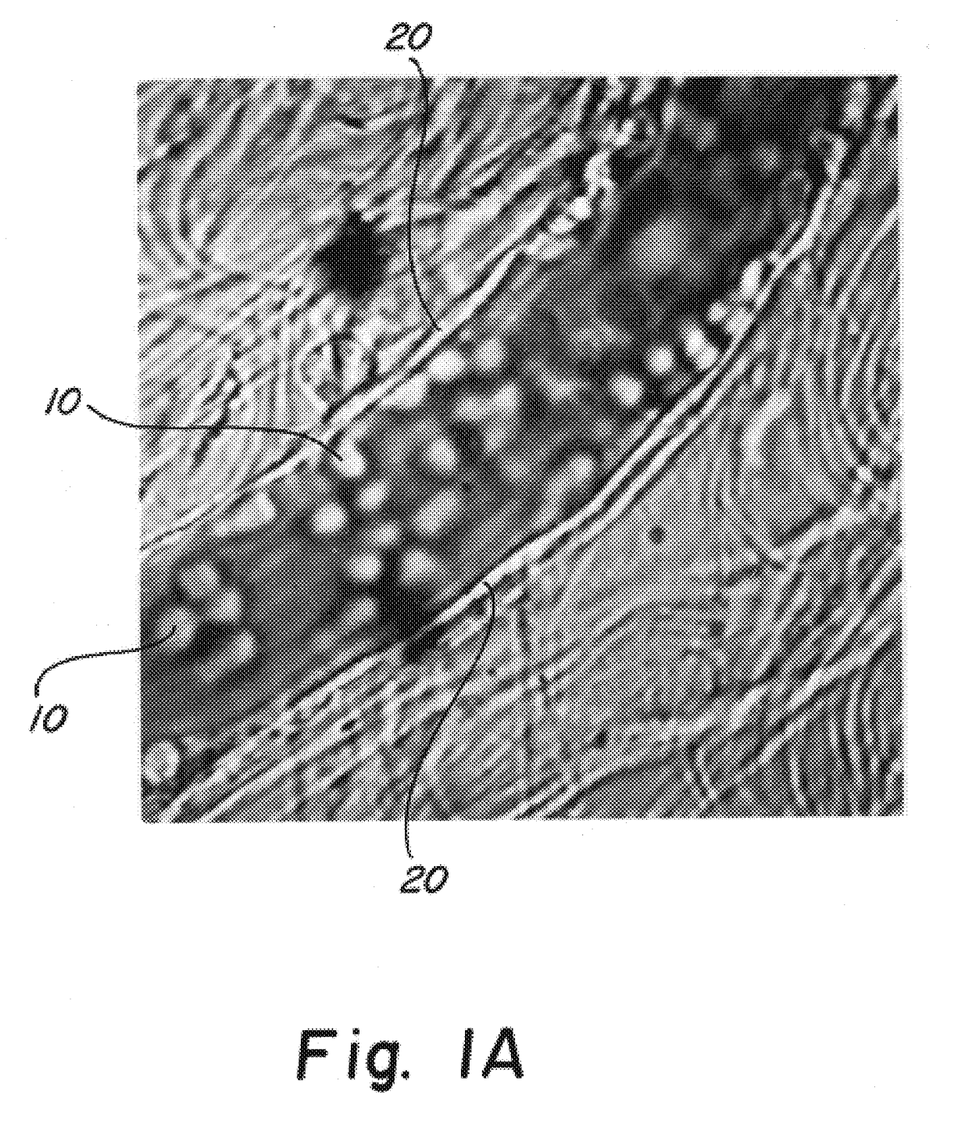
FIG. 1A is a drawing of a venule showing leukocyte adhesion.
Figure 1B:
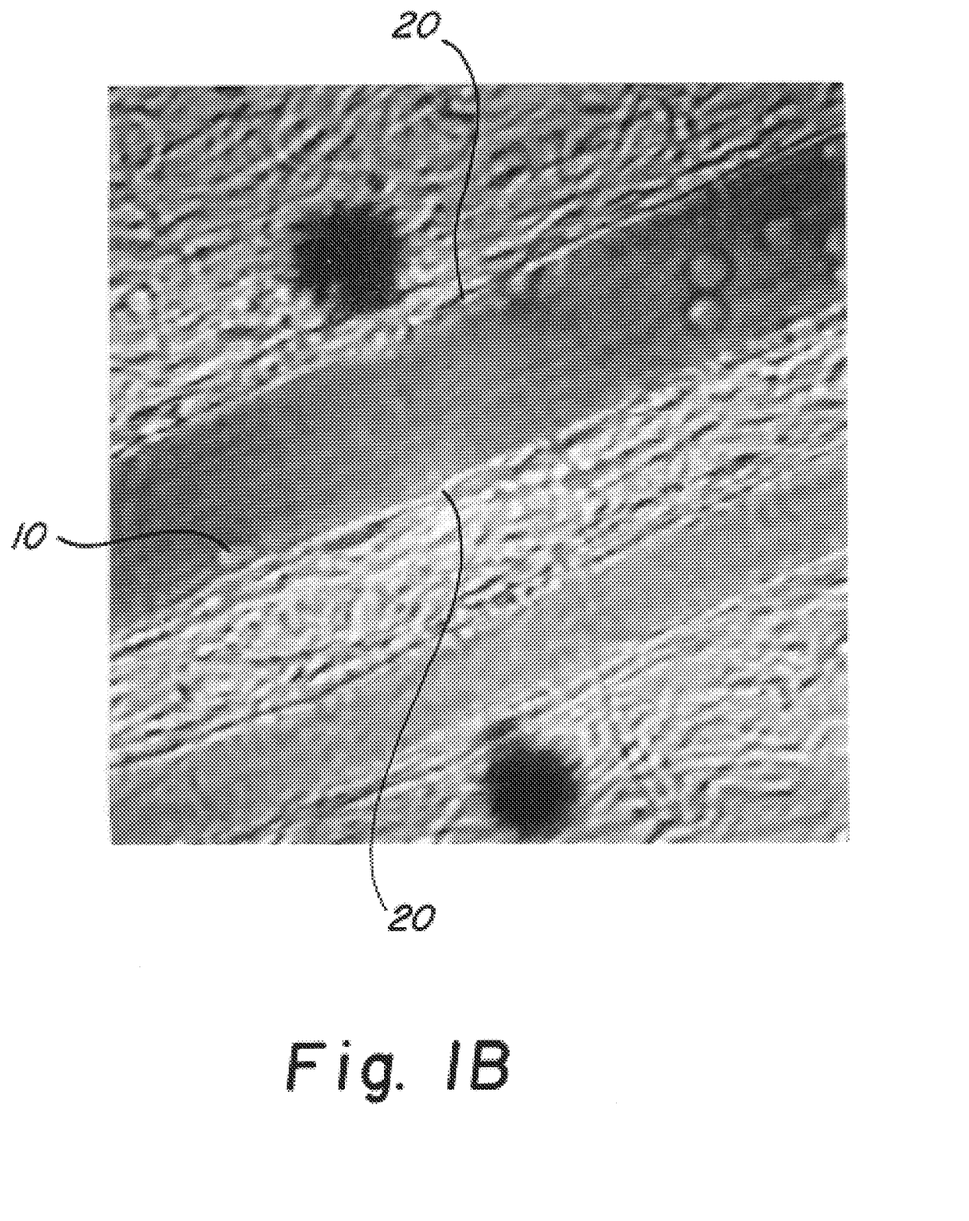
FIG. 1B is a drawing of a venule showing leukocyte rolling.
Figure 2A:
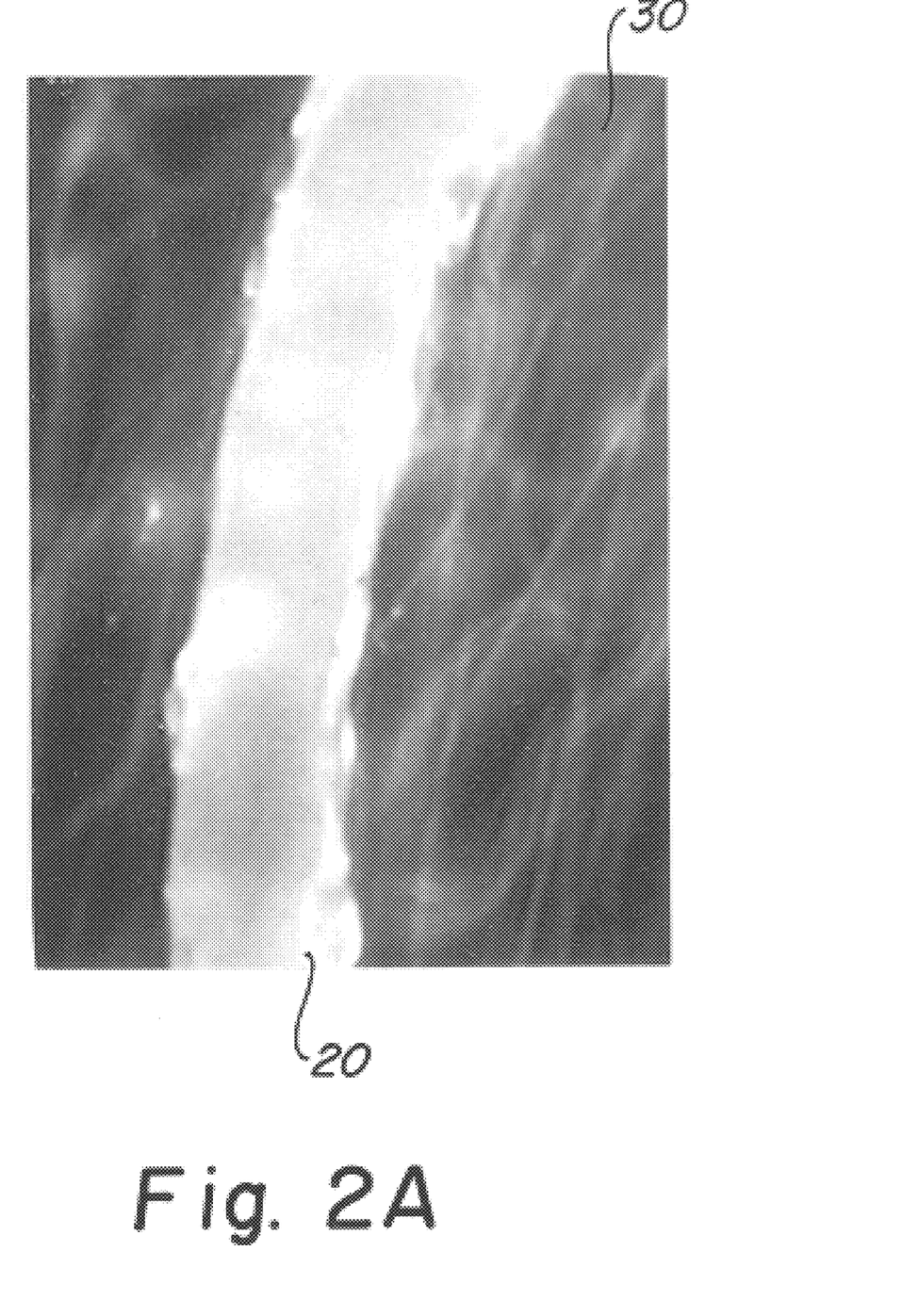
FIG. 2A is a drawing of a venule showing leakage of FITC-labeled albumin through the venule wall into the interstitial tissues.
Figure 2B:
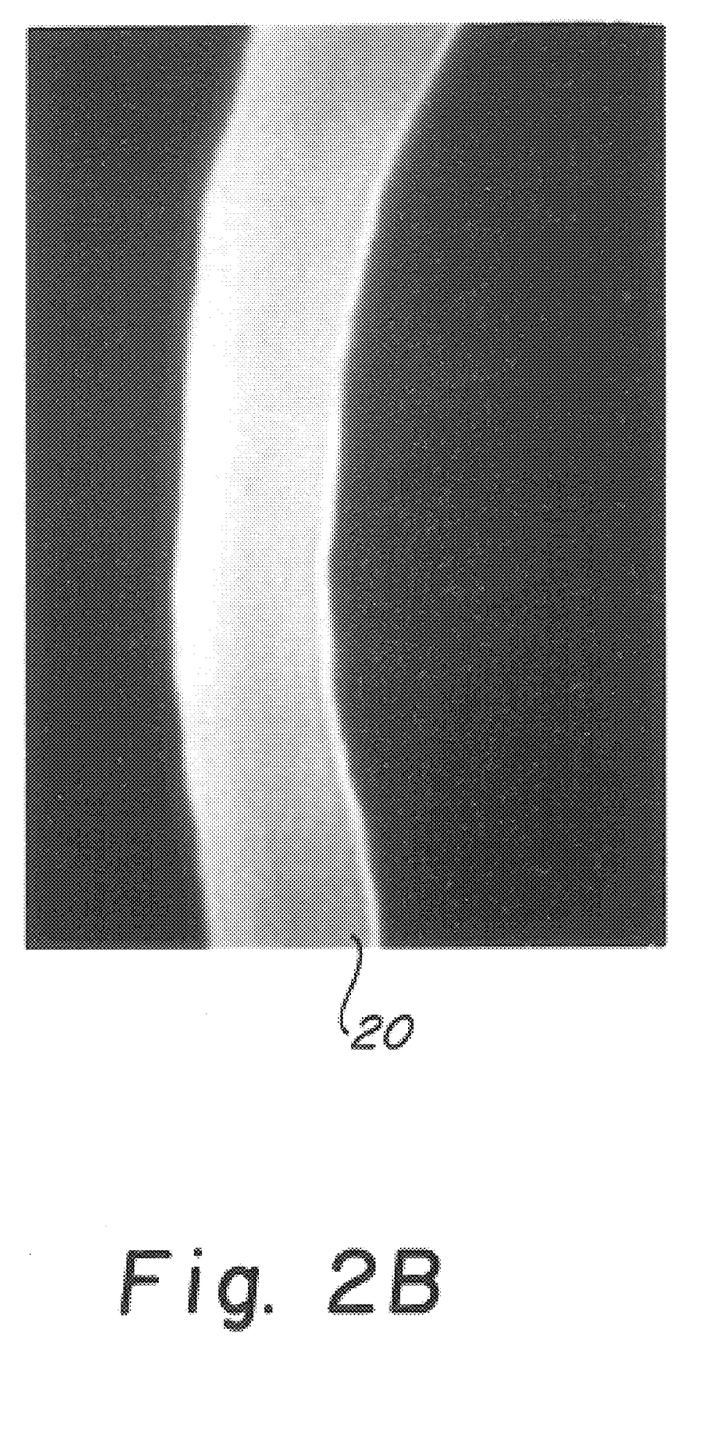
FIG. 2B is a drawing of a venule showing FITC-labeled albumin confined to a venule with no leakage into interstitial tissues.

The general preparation of the rats was the same for all demonstrative protocols discussed herein. The exposure of the intestinal mesentery for view on the inverted microscope was used only with the protocols involving study of the venules: leukocyte adhesion (FIGS. 1A and 1B) and leakage of fluorescein-labeled albumin from permeable venules (FIGS. 2A and 2B). The demonstrative protocol to show arteriolar hyperreactivity in the hemorrhagic shock model involved use of a mechanically-perfused rat stomach described below.

General Protocol for Studying Arteriolar Hyperreactivity

Using a urethane-anesthetized rat according to the general rat preparation protocol above, the abdomen was opened in the midline and the stomach was exposed. The splenic artery and vein were ligated at a point distal to the origin of the short gastric vessels, and the pancreatoduodenal and hepatic arteries were also ligated. The spleen, greater omentum, and the portion of the pancreas near the stomach were removed. A portion of the coeliac trunk (approximately 4 mm.) was carefully isolated from surrounding tissue. Heparin (1,000 u. per kg.) was given IV and the carotid artery cannula was connected to a silastic tubing passing through a variable speed peristaltic pump. A cannula at the end of was arterial circuit is inserted into the coeliac artery, which allowed the stomach to be perfused at constant flow via the gastroepiploic artery with blood from the carotid artery. With these procedures, the stomach was perfused in the living animal in situ with venous drainage occurring through normal routes. A branch from the arterial cannula to the stomach was then connected to the transducer to continuously record gastric perfusion pressure throughout the experiment.

Figure 3:
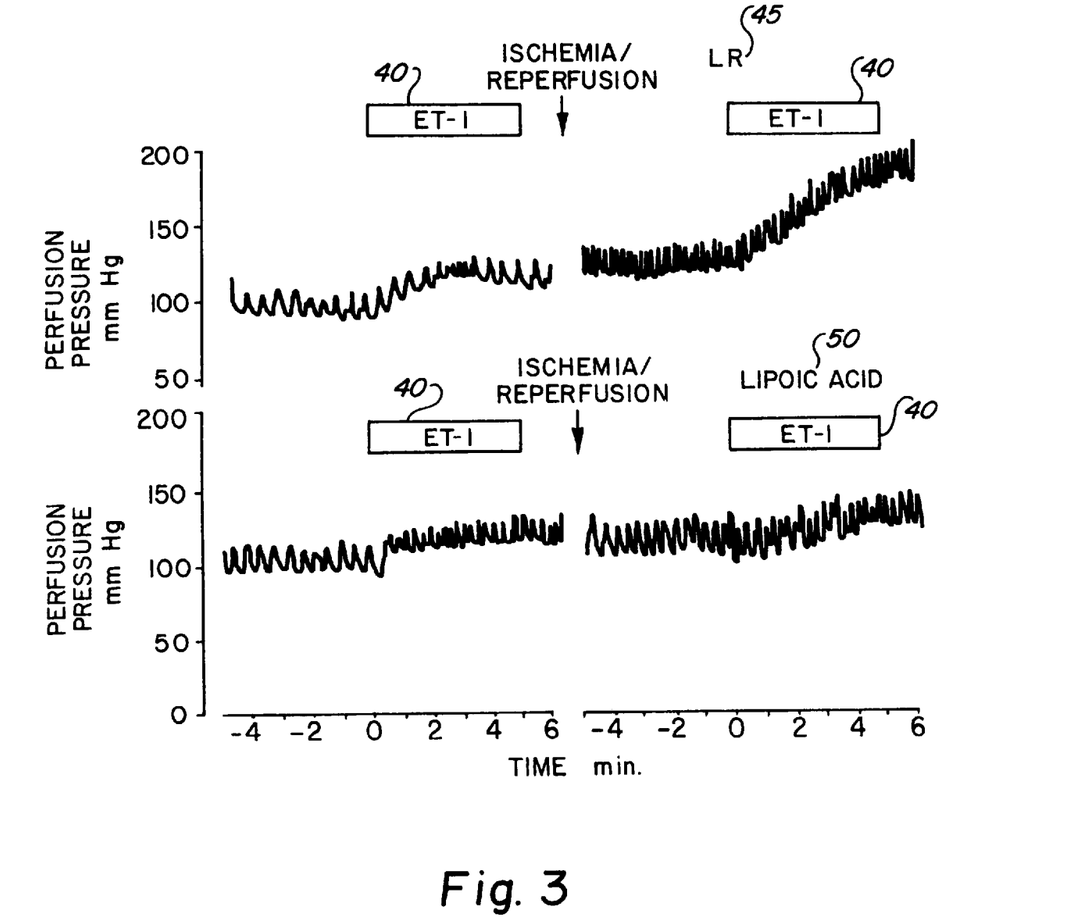
FIG. 3 is a graph of gastric perfusion pressure versus time following infusions of endothelin-1 followed by perfusion with either saline or (α-lipoic acid demonstrating enhanced arteriolar constriction in the absence of α-lipoic acid.

After the surgical preparation of the mechanically-perfused stomach was complete, the rate of the peristaltic pump was gradually increased until perfusion pressure was nearly equal to systemic arterial pressure. After this, flow to the stomach was not changed and perfusion pressure was allowed to fluctuate. Under conditions of constant flow, changes in perfusion pressure reflected changes in vascular resistance in the stomach. Vascular resistance was calculated by dividing perfusion pressure in mmHg by blood flow (normalized according to the dry weight of the stomach to eliminate variability due to differences in the extent of edema of the tissue). Changes in vascular resistance were measured during intraarterial graded doses of vasoactive agents such as endothelin-1 to the stomach for five minute periods as illustrated in FIG. 3.

Reagents were obtained from sources in the table below and used in the concentrations indicated.

| Name of substance | Manufacturing Source | Dose | Concentration Used |
|---|---|---|---|
| REAGENTS AND SOURCES | | | |
| Platelet activating factor | Sigma Chemical Company St. Louis, Missouri | | 1–100 nM topically |
| Fluoresceinated albumin (FITC-labeled albumin) | Sigma Chemical Company St. Louis, Missouri | | 50 mg. per kg. |
| Endothelin-1 (ET-1) | Peninsula Labs | | |
| Urethane anesthetic | Sigma Chemical Company St. Louis, Missouri | 1.5 gm. per kg. | |
| Bicarbonate buffered saline | Sigma Chemical Company St. Louis, Missouri | | 37° pH 7.4 |
| Aeration gas | | | 95% $N_2$ 5% $CO_2$ |
| Heparin | | 1,000 u. per kg. | |
| Normal saline | | | |
| Lactated Ringer's | | | |

| Name of Item | Source |
|---|---|
| EQUIPMENT | |
| Homeothermic blanket | Harvard Apparatus Natick, Massachusetts |
| Polyethylene cannulas (PE50) | Fisher Scientific St. Louis, Missouri |
| Digital blood pressure monitor | MicroMed, Inc. Louisville, Kentucky |
| Optical Doppler Velocimeter | Microcirculation Research Institute College Station, Texas |
| Rectal temperature probe and digital thermometer | Harvard Apparatus |
| Videocassette recorder with time date generator | JVC S VHS Recorder Fairfield, New Jersey |
| Videocamera | Hamamatsu ICCD Hamamatsu Photonic Bridgewater, New Jersey |
| Inverted microscope | Zeiss Axiovert 135 inverted microscope Thornwood, New York |
| Video caliper | Microcirculation Research Institute College Station, Texas |
| Peristaltic pump | Harvard Apparatus |
| Statistic software package | Statistix Analytical Software Tallahassee, Florida |
| Stage micrometer | Fine Science Tools Foster City, California |
| Image analysis software | NIH Image, version 1.55 |

Specific Protocols for Demonstrating Efficacy of Ultrasonicated Micellular α-Lipoic Acid and Other Antioxidants in Microvascular Dysfunction 1. Leukocyte Adhesion After the animal has been prepared according to the above protocol for leukocyte adhesion, a 30-minute stabilization period was permitted to elapse. Observations of venules were recorded during two 10-minute control periods with a 15-minute intervening period. Mesenteric venules were selected based on the following criteria: (1) straight, unbranched vessels of at least 100 micrometers; (2) a diameter of approximately 30 micrometers (acceptable range: 20–40 micrometers); (3) fewer than 10 adherent leukocytes observed within a 100-micrometer segment of the venule during control periods; and (4) no lymphatic vessel adjacent to the venule. Venular diameter was measured using a videocaliper during the experiment or later during playback of the videotape.

After a control period, blood was withdrawn via the carotid cannula to maintain systemic blood pressure at approximately 30 mmHg. Additional blood was withdrawn as necessary to maintain blood pressure at the intended shock level, and the total volume of withdrawn blood was measured at the end of the hemorrhagic shock period. After 30 or 60 minutes of shock, lactated Ringer's solution in a volume equal to three to seven times that of the volume of shed blood was given IV. Lactated Ringer's was used as a resuscitation fluid to closely approximate the clinical practice in which lactated Ringer's or normal saline are the most commonly used resuscitative fluid. Lactated Ringer's was infused at 1 ml per hour beginning after a bolus injection of same for the duration of the experiment. Groups of rats which underwent all procedures except for a period of hemorrhagic shock served as time controls. Six to eight animals per group were used to make an appropriate statistical comparison.

Adhesive interactions of leukocytes were observed for 10-minute periods as follows: (1) control; (2) at the beginning and end of hemorrhagic shock; and (3) continuously during the first 30 minutes of resuscitation, and every 30 minutes for the next two hours.

In the animals which received the inventive formulations, those animals (randomly assigned) received an IV infusion of: (1) α-lipoic acid (0. 16 mg/kg loading dose plus 0.4 mg/kg/hour; 1.6 mg/kg plus 0.4 mg/kg/hour); (2) superoxide dismutase (0.5 mg/kg/minute) plus catalase (0.5 mg/kg/minute); or (3) deferoxamine (50 mg/kg loading dose plus 10 mg/kg/hour). The rate of continuous infusion is 1 ml per hour. Animals not undergoing hemorrhagic shock are given lactated Ringer's containing the various antioxidants or metal chelators to serve as time controls.

Adhesive interactions of leukocytes with mesenteric venules were recorded over 10-minute periods at various times throughout the experiments, and analysis was done later off-line using the videotapes. FIG. 1A shows leukocyte 10 adhesion to venule walls 20 after hemorrhagic shock followed by resuscitation with lactated Ringer's solution. FIG. 1B shows some leukocyte rolling, but no adhesion after hemorrhagic shock when the resuscitation fluid contained ultrasonicated α-lipoic acid. Rolling velocity of leukocytes along the venular endothelium was calculated by measuring the time it takes for a leukocyte to move between two points 50 micrometers apart along the vessel. This distance was determined using the stage micrometer. Rolling velocity was measured for one leukocyte during each minute of the 10-minute observation periods, and then values were averaged to obtain a single estimate for this period. The total number of rolling leukocytes passing a given point in the vessel was also determined for each 10-minute observation period, and a flux of rolling leukocytes was then expressed as a number of leukocytes rolling per second. The total number of adherent leukocytes was also determined off-line by counting those leukocytes which remained stationary for longer than 30 seconds. In addition, the number of transmigrated leukocytes in the perivascular space was later determined off-line. Leukocyte migration across the venular endothelium expressed as the number of leukocytes surrounding the venule after subtracting any leukocytes in the mesentery at the start of the experiment.

2. Venular Permeability

After the animal was prepared according to the leukocyte adhesion and venular permeability protocol above, the animal was subjected to a period of hemorrhagic shock as described in the above leukocyte adhesion protocol.

In general, the technique of demonstrating venular permeability using FITC labeled albumin involves IV injection of the FITC labeled albumin 30 minutes prior to the experiment. After excitation with a 420–490 nm source, the fluorescence intensity was measured using the ICCD camera. The average intensity of FITC labeled albumin was measured using defined areas of approximately 25 micron width by 50 micron length in the surrounding perivascular space and within venules using image analysis software. Leakage of the FITC-labeled albumin marker was determined as the ratio of perivascular to intravascular fluorescence intensities.

Referring to FIG. 2A, the drawing shows a venule 20 after 60 minutes of hemorrhagic shock (blood pressure maintained at 30 mmHg as described in the leukocyte adhesion protocol above) and followed by resuscitation, taken 30 minutes after resuscitation. FIG. 2A shows increased permeability of the vessel to the FITC-labeled albumin 30.

Venular permeability to FITC-labeled albumin was measured during 10-minute periods as follows: (1) control; (2) at the beginning and end of hemorrhagic shock; and (3) continuously during the first 30 minutes after resuscitation, and then every 30 minutes for the next two hours.

After the period of hemorrhagic shock, animals were resuscitated with an IV bolus injection of lactated Ringer's in a volume equal to seven times the amount of withdrawn blood. The animals were then randomly assigned to receive either an IV infusion of: (1) lactated Ringer's; (2) α-lipoic acid (0.16 mg/kg loading dose plus 0.04 mg/kg per hour; 1.6 mg/kg loading dose plus 0.04 mg/kg per hour); (3) superoxide dismutase (0.5 mg/kg per minute) plus catalase (0.5 mg/kg per minute); or (4) deferoxamine (50 mg/kg loading dose plus 10 mg/kg/hour). The rate of infusion is 1 ml per hour. FIG. 2B shows retention of the fluorescent FITC labeled albumin within the venule after hemorrhagic shock and resuscitation with the (α-lipoic acid solution.

3. Arteriolar Dysfunction

After the animal was prepared according to the general protocol for arteriolar hyperreactivity, the animal underwent a 30-minute control period of stable gastric vascular resistance. Following the stabilization period endothelin-1 40 ($10^{-10}$–$10^{-9}$ M) (FIG. 3) or bethanechol ($10^{-7}10^{-6}$ M) was infused intraarterially to the stomach. After gastric perfusion pressure returned to baseline values, hemorrhagic shock was produced as described in the previous two specific protocols. During hemorrhagic shock, flow to the stomach was reduced by slowing the peristaltic pump until perfusion pressure was again approximately equal to the systemic blood pressure. The rats were then given lactated Ringer's in a volume equivalent to seven times the amount of withdrawn blood. The pump speed was then increased after resuscitation to the original rate under controlled conditions and then left unchanged for the duration of the protocol. Endothelin-1 or bethanechol were then infused to the stomach as given under controlled conditions at hourly intervals over the next four hours. These procedures were also performed in rats which did not undergo hemorrhagic shock to serve as time controls.

To demonstrate the effect of micellular antioxidants and chelators according to this protocol, after a period of hemorrhagic shock the animals were resuscitated with an IV injection of lactated Ringer's 45 as in the previous two protocols. The animals are then randomly assigned to receive an IV infusion of: (1) lactated Ringer's 45; (2) (α-lipoic acid 50 (0.16 mg/kg loading dose plus 0.04 mg/kg/hour; 1.6 mg/kg plus 0.04 mg/kg/hour) (FIG. 3); (3) superoxide dismutase (0.5 mg/kg/minute) plus catalase (0.5 mg/kg/minute); or (4) deferoxamine (50 mg/kg loading dose plus 10 mg/kg/hour). The rate of infusion was 1 ml per hour. Those animals which did not undergo hemorrhagic shock were given lactated Ringer's containing the various antioxidants or metal chelators to serve as time controls. Changes in gastric vascular reactivity were measured as described above in the general protocol for arteriolar dysfunction.

FIG. 3 shows that reperfusion after hemorrhagic shock (ischemia) with lactated Ringer's solution 45 is associated with abnormal vascular reactivity to endothelin-1 40 which is not seen with α-lipoic acid 50 resuscitation.

It is to be understood that while certain forms of this invention have been illustrated and described, it is not limited thereto except insofar as such limitations are included in the following claims and allowable functional equivalents thereof.

We claim:

1. A pharmaceutical composition for treating acute microvascular injury comprising an ultrasonicated formulation of α-lipoic and a parenterally acceptable aqueous solution.

2. The composition of claim 1 further comprising a pharmacologically effective amount of an additional antioxidant selected from the group consisting of catalase, superoxide dismutase, selenium, nitrones N-acetylcysteine and alpha-tocopherol.

3. The composition of claim 1 further comprising a pharmacologically effective amount of a metal chelator selected from the group consisting of deferoxamine and urates.

4. The composition of claim 1 wherein said a parenterally acceptable aqueous solution is selected from the group consisting of 0.9% saline solution, 5% dextrose solution, lactated Ringers solution, 5% dextrose in lactated Ringer's solution, dextrose-saline combinations, albumin-containing solutions, dextran, dextran-saline combinations, and stabilized hemoglobin-containing resuscitation fluids.

5. A method of preventing and/or treating acute blood vessel injury in mammals comprising parentally administering a pharmacologically effective amount of an ultrasonicated formation of α-lipoic acid and an aqueous solution.

6. The method of claim 5 wherein said formulation further comprises a pharmacologically effective amount of an additional antioxidant selected from the group consisting of catalase, superoxide dismutase, selenium, alpha-tocopherol, nitrones and N-acetylcysteine.

7. The method of claim 5 wherein said formulation further comprises a pharmacologically effective amount of a metal chelator selected from the group consisting of deferoxamine and urates.

8. The method of claim 5 wherein said aqueous solution is selected from the group consisting of 0.9% saline solution, 5% dextrose solution, lactated Ringers solution, 5% dextrose in lactated Ringer's solution, dextrose-saline combinations, albumin-containing solutions, dextran, dextran-saline combinations, and stabilized hemoglobin-containing resuscitation fluids.

9. A method for preparing a pharmaceutical formulation useful for the prevention and treatment of blood vessel injury in mammals comprising the steps of:

(a) adding α-lipoic acid to an aqueous solution; and (b) ultrasonically blending the α-lipoic acid/aqueous mixture to form a micellar suspension.

10. The method of claim 9 wherein said formulation is ultrasonically blended for about 90 to 240 seconds.

11. The method of claim 9 wherein said aqueous solution is selected from the group consisting of 0.9% saline solution, 5% dextrose solution, lactated Ringers solution, 5% dextrose in lactated Ringer's solution, dextrose-saline combinations, albumin-containing solutions, dextran, dextran-saline combinations, and stabilized hemoglobin-containing resuscitation fluids.

12. The method of claim 9 further comprising the step of adding a pharmacologically effective amount of an additional antioxidant selected from the group consisting of catalase, superoxide dismutase, selenium, alpha-tocopherol, nitrones and N-acetylcysteine.

13. The method of claim 12 wherein said additional antioxidant is ultrasonically in said aqueous solution prior to its addition to the α-lipoic acid/aqueous mixture.

14. The method of claim 9 further comprising the step of adding a pharmacologically mount of a metal chelator selected from the group consisting of deferoxamine and urates.

15. The method of claim 14 wherein said chelator is ultrasonically suspended in said aqueous solution prior to its addition to the α-lipoic acid/aqueous mixture.

16. A method for preparing a pharmaceutical formulation useful for the prevention and of blood vessel injury in mammals comprising the steps of:

(a) adding therapeutically effective amounts of α-lipoic acid, at least one additional antioxidant and at least one metal chelator to an aqueous solution; and (b) ultrasonically blending the α-lipoic acid/antioxidant/chelator/aqueous mixture to form a micellar suspension.

* * * * *

UNITED STATES PATENT AND TRADEMARK OFFICE
CERTIFICATE OF CORRECTION

PATENT NO. : 5,990,153
DATED : November 23, 1999
INVENTOR(S) : Wood et al.

It is certified that error appears in the above-identified patent and that said Letters Patent is hereby corrected as shown below:

Column 9, insert the title of the first table: "REAGENTS AND SOURCES" over the column headings rather than under; insert the title of the second table: "EQUIPMENT" over the column headings rather than under.

Column 12, line 11, delete the "(" before the word "α-lipoic"; line 17, insert a hypen between "$10^{-7}$ and $10^{-6}$ M"; line 39, delete the "(" before the word "α-lipoic".

Claim 13, column 14, line 17, insert the word -- suspended-- after the word "ultrasonically".

Claim 14, column 14, line 20, insert the word --effective-- after the word "pharmacologically"; correct the spelling of the word "amount".

Claim 16, column 14, line 27, insert the word --treatment-- after the words "prevention and".

Signed and Sealed this

Fifth Day of September, 2000

Attest:

Attesting Officer

Q. TODD DICKINSON
Director of Patents and Trademarks